United States Patent [19]
Gold

[11] Patent Number: 4,487,775
[45] Date of Patent: Dec. 11, 1984

[54] METHOD OF TREATING TRANSPLANTED TUMORS AND CANCEROUS CACHEXIA WITH QUINOLINIC DIHYDRAZIDE

[76] Inventor: Joseph Gold, 127 Edgemont Dr., Syracuse, N.Y. 13214

[21] Appl. No.: 436,781

[22] Filed: Oct. 26, 1982

Related U.S. Application Data

[60] Division of Ser. No. 940,330, Sep. 7, 1978, abandoned, which is a continuation-in-part of Ser. No. 756,647, Jan. 4, 1977, abandoned, which is a continuation of Ser. No. 565,103, Apr. 4, 1975, abandoned, which is a continuation of Ser. No. 378,665, Jul. 12, 1973, abandoned, which is a division of Ser. No. 250,883, May 8, 1972, abandoned.

[51] Int. Cl.$^3$ .................. A61K 31/455; A61K 31/655
[52] U.S. Cl. ..................................... 424/266; 424/226
[58] Field of Search ................................ 424/266, 226

*Primary Examiner*—Jerome D. Goldberg
*Attorney, Agent, or Firm*—Henry P. Stevens

[57] ABSTRACT

Quinolinic dihydrazide will inhibit the growth of various transplanted tumors such as Walker 256 carcinoma in animals when administered orally or intraperitoneally.

5 Claims, No Drawings

METHOD OF TREATING TRANSPLANTED TUMORS AND CANCEROUS CACHEXIA WITH QUINOLINIC DIHYDRAZIDE

CROSS REFERENCE TO RELATED APPLICATIONS

This application is a division of U.S. Ser. No. 940,330 filed Sept. 7, 1978 now abandoned which in turn was a continuation-in-part of U.S. Ser. No. 756,647 filed Jan. 4, 1977 now abandoned which in turn was a continuation of U.S. Ser. No. 565,103 filed Apr. 4, 1975 now abandoned which in turn was a continuation of U.S. Ser. No. 378,665 filed July 12, 1973 now abandoned which in turn was a division of U.S. Ser. No. 250,883 filed May 8, 1972 and now abandoned.

SUMMARY OF THE INVENTION

I have now discovered that the parenteral and oral administration of quinolinic dihydrazide will reduce the growth of tumors such as Walker 256 carcinoma.

DESCRIPTION OF THE PREFERRED EMBODIMENTS

Since quinolinic dihydrazide is partially soluble in water, it can be either dissolved or suspended in sterile, aqueous, isotonic, saline solution and administered orally or parenterally to mammals evincing symptoms of Walker 256 carcinoma tumor growth. Effective dosages can vary preferably from 65 to 125 mg/kg daily for about 5 days until the size of the tumor regresses. If desired, the dihydrazide can be formulated with solid carriers such as talc, corn starch or stearic acid and compressed into tablets for oral administration.

The following example sets forth the best mode contemplated for carrying out the present invention.

EXAMPLE 1

In this series of tests, the dihydrazide of quinolinic acid was compared to the dihydrazides of sebacic acid, diglycollic acid and succinic acid for their effect on tumor growth. In each instance, the compounds were either dissolved or suspended in water and injected intraperitoneally at various dosages daily for four days. The mammals used were growing female rats weighing about 70 grams each. Five rats were used at each dosage level and ten rats served as controls.

On day 1, five million cells of Walker 256 intramuscular carcinoma in a volume of 0.2 ml. were injected into one thigh of each rat. On days 3–6, treatment was administered intraperitoneally at the dosage specified. On day 7, the animals were sacrificed and both lower extremities were removed. The difference in weight between the tumor thigh and the contralateral thigh was used as the weight of the tumor. Weights at the beginning and end of each test were indicative of possible drug toxicity and recorded as average weight change (AWC) or the net animal weight gain or loss minus the weight of the tumor. All animals were maintained on standard laboratory chow and water. Tumor inhibition was measured as T/C or the ratio of the tumor weight of the treated animals divided by the tumor weight of the control animals. The results are shown in the table below wherein the percent inhibition is the reciprocal of the T/C value.

| Acid Di-hydrazide | Dosage mg/kg | AWC in Grams Con. | AWC in Grams Treated | Tumor Response in Grams % Tumor Controls | Tumor Response in Grams % Tumor Treated | Tumor Response in Grams % Tumor Inhibition |
|---|---|---|---|---|---|---|
| Quinolinic | 125 | 8.0 | 19.4 | 9.8 | 1.4 | 86 |
|  | 65 | 8.0 | 2.1 | 9.8 | 4.5 | 54 |
| Sebacic | 125 | 5.2 | 16.4 | 8.8 | 2.6 | 70 |
| Diglycollic | 750 | 8.0 | 26.2 | 9.8 | 0.6 | 94 |
|  | 500 | 8.0 | 17.2 | 9.8 | 2.4 | 76 |
|  | 250 | 8.0 | 0.1 | 9.8 | 5.1 | 48 |
| Succinic | 500 | 8.0 | 29.9 | 9.8 | 0.7 | 93 |
|  | 250 | 8.0 | 13.3 | 9.8 | 3.1 | 68 |
|  | 125 | 8.0 | 4.3 | 9.8 | 6.1 | 38 |

There were no deaths at any of the dosages employed which shows that toxicity as a function of mortality was virtually zero. From the foregoing data, it is apparent that quinolinic acid dihydrazide and sebacic acid dihydrazide were potent inhibitors of tumor growth at a dosage of 125 mg/kg whereas much larger dosages of succinic acid and diglycollic acid dihydrazide were required in order to achieve the same percentage of tumor inhibition.

What I claim is:

1. A method of treating a transplanted Walker 256 carcinoma tumor in a quadruped so afflicted which comprises internally administering thereto quinolinic dihydrazide in an effective dosage sufficient to inhibit the growth of said tumor.

2. A method as in claim 1 in which the dihydrazide is administered parenterally.

3. A method as in claim 1 in which the dihydrazide is administered at a dosage of about 65 to 125 mg/kg of body weight daily.

4. A method as in claim 1 in which the dihydrazide is administered for at least 4 days.

5. A method as in clam 1 in which the dihydrazide is administered orally in dosage form admixed with a pharmaceutically acceptable carrier.

* * * * *